United States Patent [19]

Smith

[11] 4,211,714

[45] Jul. 8, 1980

[54] 2,2-DIFLUORO-TRANS-4,5,13,14-TETRAHYDRO-PGI₁ COMPOUNDS

[75] Inventor: Herman W. Smith, Kalamazoo Township, Kalamazoo County, Mich.

[73] Assignee: The Upjohn Company, Kalamazoo, Mich.

[21] Appl. No.: 915,349

[22] Filed: Jun. 14, 1978

Related U.S. Application Data

[63] Continuation-in-part of Ser. No. 821,536, Aug. 3, 1977.

[51] Int. Cl.² .................................................. C07D 307/93
[52] U.S. Cl. ............................ 260/346.73; 260/346.22; 542/426

[58] Field of Search ..................... 260/346.22, 346.73; 542/426

[56] References Cited

PUBLICATIONS

Fried et al., Proc. Natl. Acad. Sci. 74, 2199, 1977.

*Primary Examiner*—Henry R. Jiles
*Assistant Examiner*—Bernard Dentz
*Attorney, Agent, or Firm*—Robert A. Armitage

[57] ABSTRACT

The present invention relates to certain structural and pharmacological analogs of prostacyclin (PGI₂) which are 2,2-difluoro-trans-4,5,13,14-tetradehydro-PGI₁ compounds. These novel pharmacological agents are useful as smooth muscle stimulators.

27 Claims, No Drawings

2,2-DIFLUORO-TRANS-4,5,13,14-TETRAHYDRO-PGI$_1$ COMPOUNDS

CROSS REFERENCE TO RELATED APPLICATION

The present application is a continuation-in-part application of Ser. No. 821,536, filed Aug. 3, 1977, now pending issuance as a U.S. Patent.

The present invention relates to prostacyclin analogs, for which the essential material constituting disclosure therefor is incorporated by reference here from Ser. No. 821,541, filed Aug. 3, 1977, now U.S. Pat. 4,109,082, issued Aug. 22, 1978.

I claim:

1. A prostacyclin analog of the formula

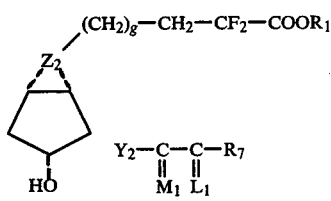

wherein $Y_2$ is —C≡C—.
wherein $Z_2$ is

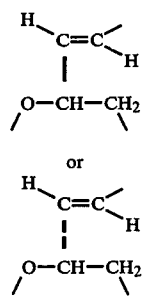

wherein g is the integer zero, one, or 2;
wherein $M_1$ is

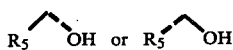

wherein $R_5$ is hydrogen or alkyl with one to 4 carbon atoms, inclusive;
wherein $L_1$ is

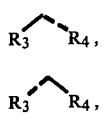

or a mixture of

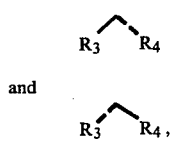

wherein $R_3$ and $R_4$ are hydrogen, methyl, or fluoro, being the same or different, with the proviso that one of $R_3$ and $R_4$ is fluoro only when the other is hydrogen or fluoro;

wherein $R_1$ is hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, two or three chloro or alkyl of one to 3 carbon atoms; phenyl substituted in the para position by

 (a)

 (b)

 (c)

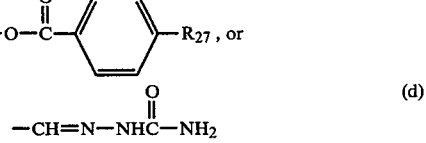 (d)

wherein $R_{25}$ is methyl, phenyl, acetamidophenyl, benzamidophenyl, or —NH$_2$; $R_{26}$ is methyl, phenyl, —NH$_2$, or methoxy; and $R_{27}$ is hydrogen or acetamido; phenacyl, i.e., $$-CH_2-\underset{\underset{O}{\|}}{C}-\text{phenyl};$$

phenacyl substituted in the para position by chloro, bromo, phenyl, or benzamido; or a pharmacologically acceptable cation;
wherein $R_7$ is —(CH$_2$)$_m$—CH$_3$, (1)

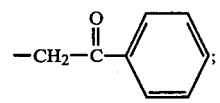, or (2)

(3)

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl.

2. A prostacyclin analog according to claim 1, wherein $Z_2$ is a mixture of 3. 2,2-Difluoro(6RS)-trans-4,5,13,14-tetradehydro-PGI$_1$, a prostacyclin analog according to claim 2.

4. A prostacyclin analog according to claim 1, wherein $Z_2$ is

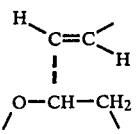

5. 2,2-Difluoro-trans-4,5,13,14-tetradehydro-6α-PGI$_1$, a prostacyclin analog according to claim 4.
6. 2,2-Difluoro-15-methyl-trans-4,5,13,14-tetradehydro-6α-PGI$_1$, a prostacyclin analog according to claim 4.
7. 2,2-Difluoro-16,16-dimethyl-trans-4,5,13,14-tetradehydro-6α-PGI$_1$, a prostacyclin analog according to claim 4.
8. 2,2,16,16-Tetrafluoro-trans-4,5,13,14-tetradehydro-6α-PGI$_1$, a prostacyclin analog according to claim 4.
9. A prostacyclin analog according to claim 1, wherein $Z_2$ is

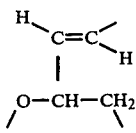

10. A prostacyclin analog according to claim 9, wherein g is zero.
11. A prostacyclin analog according to claim 10, wherein

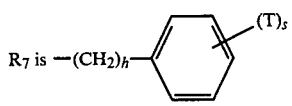

12. 2,2-Difluoro-17-phenyl-18,19,20-trinor-trans-4,5,13,14-tetradehydro-6β-PGI$_1$, a prostacyclin analog according to claim 11.

13. A prostacyclin analog according to claim 10, wherein

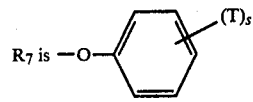

14. 2,2-Difluoro-16-phenoxy-17,18,19,20-tetranor-trans-4,5,13,14-tetradehydro-6β-PGI$_1$, a prostacyclin analog according to claim 13.
15. A prostacyclin analog according to claim 10, wherein $R_7$ is —(CH$_2$)$_m$—CH$_3$—.
16. A prostacyclin analog according to claim 15, wherein $R_5$ is methyl.
17. 2,2-Difluro-15-methyl-trans-4,5,13,14-tetradehydro-6β-PGI$_1$, a prostacyclin analog according to claim 16.
18. A prostacyclin analog according to claim 15, wherein $R_5$ is hydrogen.
19. A prostacyclin analog according to claim 18, wherein at least one of $R_3$ and $R_4$ is fluoro.
20. 2,2,16,16-Tetrafluoro-trans-4,5,13,14-tetradehydro-6β-PGI$_1$, a prostacyclin analog according to claim 19.
21. A prostacyclin analog according to claim 18, wherein at least one of $R_3$ and $R_4$ is methyl.
22. 2,2-Difluoro-16,16-dimethyl-trans-4,5,13,14-tetradehydro-6β-PGI$_1$, a prostacyclin analog according to claim 21.
23. A prostacyclin analog according to claim 18, wherein $R_3$ and $R_4$ are both hydrogen.
24. 2,2-Difluoro-trans-4,5,13,14-tetradehydro-6β-PGI$_1$, methyl ester, a prostacyclin analog according to claim 23.
25. 2,2-Difluoro-trans-4,5,13,14-tetradehydro-6β-PGI$_1$, tris(hydroxymethyl)amino methane salt, a prostacyclin analog according to claim 23.
26. 2,2-Difluoro-trans-4,5,13,14-tetradehydro-6β-PGI$_1$, adamantanamine salt, a prostacyclin analog according to claim 23.
27. 2,2-Difluoro-trans-4,5,13,14-tetradehydro-6β-PGI$_1$, a prostacyclin analog according to claim 23.

* * * * *

UNITED STATES PATENT OFFICE
CERTIFICATE OF CORRECTION

Patent No. 4,211,714　　　　　　　　　　Dated 8 July 1980

Inventor(s) Herman W. Smith

It is certified that error appears in the above-identified patent and that said Letters Patent are hereby corrected as shown below:

Column 1, lines 20-26, that portion of the formula reading

 should read 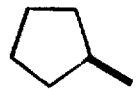

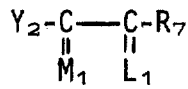 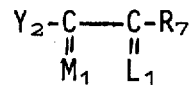

Signed and Sealed this

Seventh Day of April 1981

[SEAL]

Attest:

RENE D. TEGTMEYER

*Attesting Officer*　　　*Acting Commissioner of Patents and Trademarks*